US005543383A

United States Patent [19]
Parker et al.

[11] Patent Number: 5,543,383
[45] Date of Patent: Aug. 6, 1996

[54] HERBICIDAL COMPOSITIONS COMPRISING SOLUTIONS OF GLYPHOSATE AND POLYUREA AND/OR POLYURETHANE

[75] Inventors: Brian A. Parker, Nashua, N.H.; Longin V. Holejko, Arlington, Mass.

[73] Assignee: Hampshire Chemical Corp., Lexington, Mass.

[21] Appl. No.: 368,204

[22] Filed: Dec. 30, 1994

[51] Int. Cl.$^6$ .......................... A01N 25/02; A01N 25/30; A01N 57/04
[52] U.S. Cl. .......................... 504/116; 504/127; 504/128; 504/206; 71/DIG. 1
[58] Field of Search .................. 504/206, 127, 504/128, 143, 116; 71/DIG. 1

[56] References Cited

U.S. PATENT DOCUMENTS

| | | | |
|---|---|---|---|
| 4,405,360 | 9/1983 | Cardarelli | 71/117 |
| 4,405,531 | 9/1983 | Franz | 260/501.12 |
| 4,761,176 | 8/1988 | Alt | 71/118 |
| 4,886,866 | 12/1989 | Braatz et al. | 528/59 |
| 4,936,901 | 6/1990 | Surgant, Sr. et al. | 71/92 |
| 5,059,704 | 10/1991 | Petroff et al. | 71/DIG. 1 |
| 5,091,176 | 2/1992 | Braatz et al. | 424/78.17 |
| 5,118,338 | 6/1992 | Moller | 71/86 |
| 5,180,414 | 1/1993 | Darchy et al. | 504/206 |
| 5,196,044 | 3/1993 | Caulder et al. | 504/127 |
| 5,258,359 | 11/1993 | Kassebaum et al. | 71/DIG. 1 |
| 5,362,705 | 11/1994 | Moucharafieh et al. | 504/206 |

*Primary Examiner*—S. Mark Clardy
*Attorney, Agent, or Firm*—Nields & Lemack

[57] ABSTRACT

A herbicidal composition including isocyanate capped high molecular weight diols, triols and polyols. Glyphosate and/or a herbicidally active derivative thereof such as a glyphosate salt is combined with hydrophilic isocyanate endcapped prepolymers in order to significantly improve the efficacy of the herbicide. A combination of surfactant, glyphosate, and a hydrated polymer or hydrophilic prepolymer consisting of isocyanate capped prepolymers which are substantially comprised of ethylene oxide, propylene oxide or butylene oxide units or a combination thereof demonstrates increased efficacy over conventional glyphosate formulations. The liquid herbicidal compositions of the present invention can be prepared by simply mixing the various constituents. The order of addition can be used effectively to cap free isocyanate groups in the hydrophilic prepolymer.

17 Claims, 3 Drawing Sheets

HERBICIDAL COMPOSITIONS COMPRISING SOLUTIONS OF GLYPHOSATE AND POLYUREA AND/OR POLYURETHANE

BACKGROUND OF THE INVENTION

Glyphosate, or N-phosphonomethylglycine ($HOOCCH_2NHCH_2PO(OH)_2$), is a well-known translocated, postemergence, broadspectrum herbicide. The typical commercial formulation contains about 41% of the isopropylamine salt of glyphosate and is believed to contain about 12% by weight of a tallow amine ethoxylate surfactant. Glyphosate is a relatively insoluble acid, and thus is typically formulated and applied as a salt, such as the isopropylamine, sodium or ammonium salt.

Surfactants are typically incorporated into the formulation to improve the activity of the glyphosate. However, the term "surfactant" is ambiguous, as the form supplied by manufacturers is not necessarily a single compound, but can be a mixture. For example, with ethoxylated surfactants, the degree of ethoxylation can be and typically is a statistical mixture. The literature describes use of surfactants in glyphosate compositions and in particular, *Weed Science,* Vol. 25, pp 275–287 (1977) demonstrates the necessity of including a surfactant in glyphosate formulations. Conventional glyphosate formulations include the use of surfactants such as silicone to enhance the rainfast properties of glyphosate formulations. However, commercialization of such formulations has been hindered by the cost of incorporation of such surfactants into the formulations, and by the hydrolytic instability of such adjuvants. Other formulations including surfactants are disclosed in U.S. Pat. Nos. 5,362,705, 5,180,414 and 5,118,338.

In addition, in view of the recent environmental concerns surrounding the use of chemical herbicides and the possibility that residuals thereof might contaminate food, ground water, etc., a substantial reduction in the amount of herbicide necessary to be effective would be highly desirable.

It is therefore an object of the present invention to improve the rainfast properties of glyphosate formulations without the use of silicone surfactants.

It is a further object of the present invention to enhance the efficacy of glyphosate formulations in an environmentally friendly manner.

SUMMARY OF THE INVENTION

The problems of the prior art have been solved by the present invention, which relates to a herbicidal composition including isocyanate capped high molecular weight diols, triols and polyols. More specifically, the present invention relates to a herbicidal composition in which glyphosate and/or a herbicidally active derivative thereof such as a glyphosate salt is combined with hydrophilic isocyanate end-capped prepolymers in order to significantly improve the efficacy of the herbicide. A combination of surfactant, glyphosate, and a hydrated polymer or hydrophilic prepolymer consisting of isocyanate capped prepolymers which are substantially comprised of ethylene oxide, propylene oxide or butylene oxide units or a combination thereof demonstrates increased efficacy over conventional glyphosate formulations. The herbicidal compositions of the present invention also exhibit controlled release of glyphosate, thereby enhancing its herbicidal efficacy. The liquid herbicidal compositions of the present invention can be prepared by simply mixing the various constituents. The order of addition can be used effectively to cap free isocyanate groups in the hydrophilic prepolymer. Hydrophilic prepolymers consisting of isocyanate capped prepolymers which are substantially comprised of ethylene oxide, propylene oxide or butylene oxide units or a combination thereof are described in the art as hydratable or water soluble. See Braatz et al., U.S. Pat. Nos. 4,886,866 and 5,091,176, the disclosure of which are hereby incorporated by reference. In one embodiment, the water soluble prepolymer can be covalently bonded to the amine group in glyphosate. In other embodiments, the prepolymer can be reacted with water to form polyurethane and polyurea-urethane polymer gels prior to the incorporation of glyphosate as the salt or acid. In a still further embodiment, the prepolymer can form a reaction product with a surfactant via a covalent linkage between the isocyanate groups of the prepolymer and a reactive group on the surfactant.

DETAILED DESCRIPTION OF THE INVENTION

Figure 1:
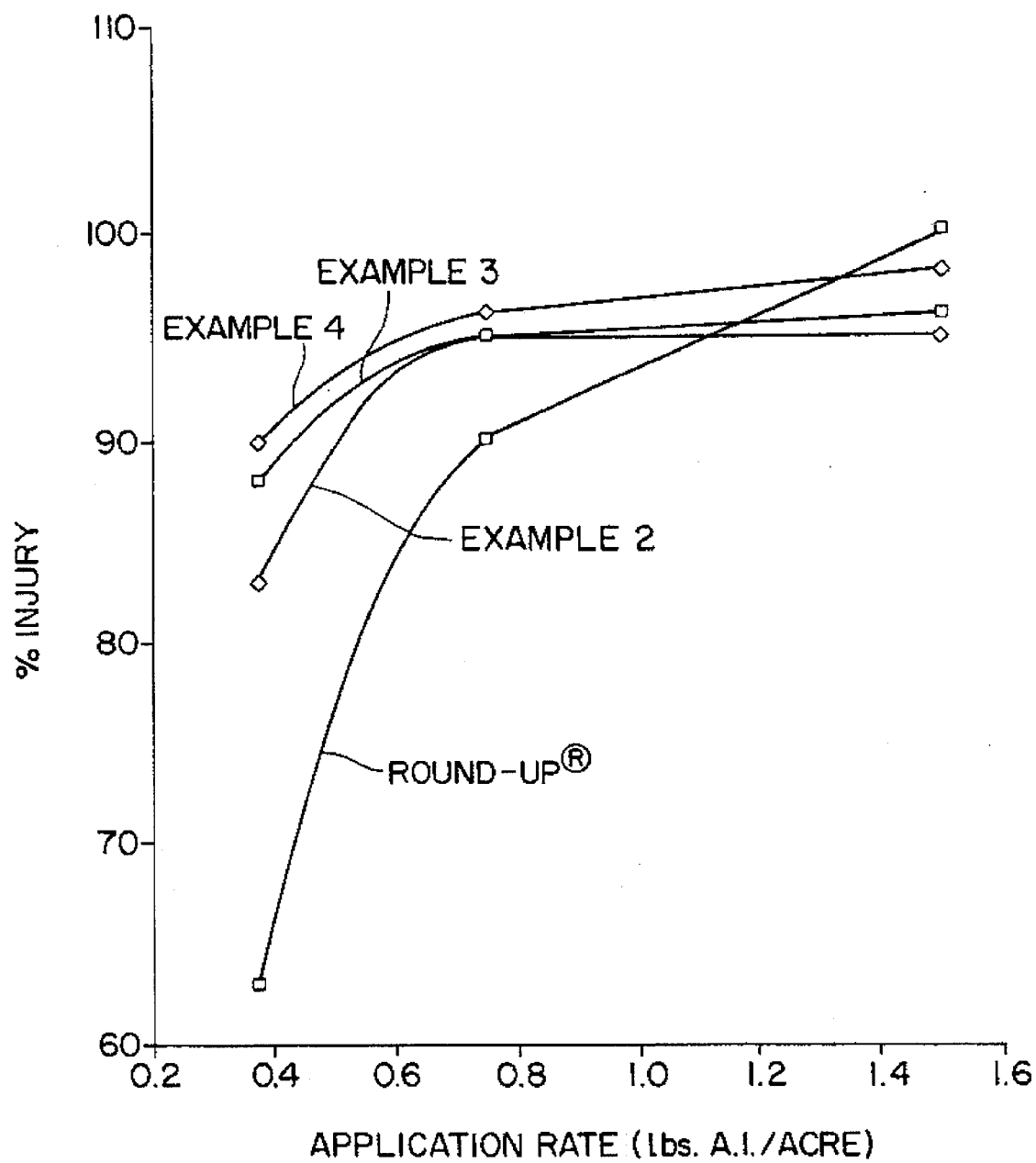
FIG. 1 is a graph comparing dose response of formulations of the present invention to commercial grade Round-up® herbicide after 28 days.

Glyphosate and its herbicidally active derivatives, particularly its salts, can be prepared by a variety of oxidations of PMIDA that are well known in the art. For example, U.S. Pat. No. 3,954,848 discloses the production of glyphosate by the acid catalyzed oxidation-hydrolysis of PMIDA. Specifically, PMIDA is mixed with water and an acid and is heated to an elevated temperature. An oxidizing agent such as hydrogen peroxide is then added to convert the PMIDA to glyphosate, which is then isolated by precipitation. U.S. Pat. No. 3,969,398 discloses the oxidation of PMIDA to glyphosate employing a molecular oxygen-containing gas such as air, oxygen, oxygen diluted with helium, argon nitrogen or other inert gases, oxygen-hydrocarbon mixtures, etc., and employing activated carbon as the catalyst. U.S. Pat. No. 4,147,719 discloses the production of certain mono- and di-salts of glyphosate in a single aqueous reaction system by oxidizing a salt of PMIDA with a molecular oxygen-containing gas in the presence of platinum supported on an activated carbon substrate. The oxidation reaction is conducted at super-atmospheric pressures in the range of 1.5 to 5 $kg/cm^2$ or higher. U.S. Pat. No. 4,898,972 discloses the production of glyphosate by the oxidation of PMIDA using a salt of cobalt or manganese in the presence of bromide ions. U.S. Pat. No. 4,002,672 discloses the production of glyphosate and salts thereof by the acid catalyzed hydrolysis of PMIDA. PMIDA is contacted with a strong acid having a pKa of less than 2.2, at an elevated temperature so as to cause the decomposition or hydrolysis of the phosphonomethyl iminodiacetic acid into N-phosphonomethyl-glycine and other decomposition products. U.S. Pat. No. 4,696,772 discloses how the activity of the activated carbon catalyst can be enhanced by first removing oxides of carbon from the surface of the carbon. Any of these methods can be used to produce the starting glyphosate acid for the present invention.

A variety of different herbicides also can be incorporated into the formulations of the present invention. Such herbicides include phenoxy acids (acids, esters, salts), benzoic acid, aryloxy phenoxypropionate (acids, ester, salts), sulfonyl ureas (acids, esters), imidazilinones, bipyridillium, diphenyl ether (acids, salts), cyclohexanedione, methane arsonate, triazines, aliphatic carboxylic acids, benzonitrile, carbamate, thiocarbamate, PYRAZONE, GLUFOSINATE, DESMEDIPHAM, TRICLOPYR, CLOPYRALID, QUINCLORAC, ETHIOZIN, PICHLORAM, BENTAZON, AMITROLE, METRIBUZIN, and PHENMEDIPHAM.

Suitable surfactants or wetting agents are those conventional in the art, as described in U.S. Pat. No. 3,853,530, the disclosure of which is hereby incorporated by reference. Such surfactants include alkyl benzene and alkyl naphthalene sulfonates, alkyl phenol polyoxyethylene, sulfated fatty alcohols, amines or acid amides, long chain acid esters of sodium isethionate, esters of sodium sulfosuccinate, sulfated or sulfonated fatty acid esters petroleum sulfonates, N-acyl sarcosinates, alkyl polyglycosides, alkyl ethoxylated amines such as tallow amine ethoxylate, etc. The surfactants may also include additives such as glycols including polyethylene glycol, diethylene glycol, ethylene glycol, alcohols such as methanol, ethanol, 2-propanol, n-propanol, butanol, hexanol and heptanol, etc. and mixtures of the aforementioned additives. A preferred surfactant is a mixture of about 1–100% (most preferably 50–100%) tallow amine ethoxylate, 1–50% polyethylene glycol, and 0–50% ethylene and diethylene glycol.

The prepolymers used as a starting material in the instant invention provide hydrated polyurethane, polyurea-urethane and polyurea polymer gels. Numerous polyurethane polymers have been previously identified. Many hydrogel polymers, prepared from various prepolymers, have been prepared and used for a wide variety of applications. Typically, hydrogels are formed by polymerizing a hydrophilic monomer in an aqueous solution under conditions such that the prepolymer becomes crosslinked, forming a three-dimensional polymeric network which gels the solution in concentrated form. Polyurethane hydrogels are formed by polymerization of isocyanate-end capped prepolymers to create urea and urethane linkages. More specifically, the prepolymers are prepared from solutions of high molecular weight isocyanate end-capped prepolymers substantially or exclusively comprised of ethylene oxide, propylene oxide or butylene oxide units, or mixtures thereof. Preferably the prepolymers are derived from polymeric monomer units (the prepolymer units) at least 75% of which are oxyethylene-based diols or polyols having molecular weights of about 100 to about 30,000, preferably 7000 to 30,000, with essentially all of the hydroxyl groups of these diols or polyols capped with polyisocyanate. Suitable polyols include triols such as glycerol, trimethylol-propane, trimethylolethane and triethanolamine. The prepolymers useful in the invention are prepared by reacting the selected diols, triols or polyols with polyisocyanate at an isocyanate-to-hydroxyl ratio of about 1.8 to about 2.2 so that essentially all of the hydroxyl groups are capped with polyisocyanate. Aromatic, aliphatic or cycloaliphatic polyisocyanates may be used. The use of aliphatic polyisocyanates permits a greater degree of handling and/or shaping since aliphatic isocyanate-capped prepolymers typically require about 20 to 90 minutes to gel to a hydrated polymer state. Prepolymers capped with aromatic polyisocyanates gel more rapidly, in about 30 to 60 seconds. Aliphatic polyisocyanates are also preferred in view of decreased toxicological considerations. Examples of suitable di- and polyfunctional isocyanates are as follows: toluene-2,4-diisocyanate, toluene-2,6-diisocyanate, commercial mixtures of toluene-2,4 and 2,6-diisocyanate, isophorone diisocyanate, ethylene diisocyanate, ethylidene diisocyanate, propylene-1,2-diisocyanate, cyclohexylene-1,2-diisocyanate, cyclohexylene-1,4-diisocyanate, m-phenylene diisocyanate, 3,3"-diphenyl-4,4"-biphenylene diisocyanate, 1,6-hexamethylene diisocyanate, 1,4-tetramethylene diisocyanate, 1,10-decamethylene diisocyanate, cumene-2,4diisocyanate, 1,5-naphthalene diisocyanate, methylene dicyclohexyl diisocyanate, 1,4-cyclohexylene diisocyanate, p-tetramethyl xylylene diisocyanate, p-phenylene diisocyanate, 4-methoxy-1,3-phenylene diisocyanate, 4-chloro-1,3-phenylene diisocyanate, 4-bromo-1,3-phenylene diisocyanate, 4-ethoxy-1,3-phenylene di-isocyanate, 2,4-dimethyl-1,3-phenylene diisocyanate, 2,4-dimethyl-1,3-phenylene diisocyanate, 5,6-dimethyl-1,3phenylene di-isocyanate, 2,4-diisocyanatodiphenylether, 4,4"-diisocyanatodiphenylether, benzidine diisocyanate, 4,6-dimethyl-1,3-phenylene diisocyanate, 9,10-anthracene diisocyanate, 4,4"-diisocyanatodi-benzyl, 3,3"-dimethyl-4,4"-diisocyanatodiphenylmethane, 2,6-dimethyl-4,4"-diisocyanatodiphenyl, 2,4-diisocyanatostilbene, 3,3"-dimethoxy-4,4"-diisocyanatodiphenyl, 1,4-antracenediisocyanate, 2,5-fluorenediisocyanate, 1,8-naphthalene diisocyanate, 2,6-diisocyanatobenzfuran, 2,4,6-toluene triisocyanate, p,p',p"-triphenylmethane triisocyanate, trifunctional trimer (isocyanurate) of isophorone diisocyanate, trifunctional biuret of hexamethylene diisocyanate, trifunctional trimer (isocyanurate) of hexamethylene diisocyanate, polymeric 4,4"-diphenylmethane diisocyanate, xylylene diisocyanate and m-tetramethyl xylylene diisocyanate.

Capping of the selected diols or polyols with polyisocyanates to form prepolymers for use in the present invention is effected using stoichiometric amounts of reactants. The isocyanate-to-hydroxyl group ratio should be between about 0.01 and about 10, preferably 0.1 to 3, most preferably 0.2 to 2.2. Higher ratios may be used but are not preferred since they may lead to problems associated with excessive monomer present in the final products. The capping reaction may be by any convenient method or procedure, such as at about 20° to about 150° C., under dry nitrogen, for about 2 hours to about 14 days, preferably in the absence of a catalyst. The preferred temperature is about 60° to 100° C. The reaction is terminated when the isocyanate concentration approximates theoretical values.

Preferred prepolymers include toluene diisocyanate-polyethylene glycol-timethylolpropane, methylene diisocyanate-methylene diisocyanate homopolymer-polymeric methylene diisocyanate -polyethylene glycol, toluene diisocyanate and polymer of ethylene oxide and propylene oxide with trimethylolpropane, isophorone diisocyanate and polymer of ethylene oxide-propylene oxide-trimethylolpropane, toluene diisocyanate polyethylene glycol trilactate, and polyethylene glycol end capped with toluene diisocyanate. Such prepolymers are available under the tradename HYPOL® from Hampshire Chemical Corp., and include HYPOL® PreMA®, HYPOL® 2000, HYPOL® 3000, HYPOL® 4000, HYPOL® 5000, and biodegradable HYPOL®.

Preferably the ratio of glyphosate to prepolymer is from about 0.001 to about 5.

Neutralization of the glyphosate acid to form a herbicidally active glyphosate derivative can be effectuated with any suitable base, including alkali metal, alkali earth metal and ammonium hydroxides and alkyl amines. Preferred glyphosate salts upon neutralization include the mono(trimethylamine) salt of N-phosphonomethylglycine, the mono(diethylenetriamine) salt of N-phosphonomethylglycine, the monoisopropylamine salt of N-phosphonomethylglycine, the mono-n-propylamine salt of N-phosphonomethylglycine, the mono(tallowamine) salt of N-phosphonomethylglycine, the monosodium salt of N-phosphonomethylglycine and the monopotassium salt of N-phosphonomethylglycine. Those skilled in the art will readily appreciate that the corresponding di- and tri-salts of N-phosphonomethylglycine also can be prepared by increasing the amount of base added accordingly.

In the first embodiment of the present invention, the prepolymer can be incorporated into solution as a reaction product with water. The amount of prepolymer used should be low enough so as to avoid immediate gel formation. Generally less than about 20% by weight is suitable, more preferably about 2 to 10% by weight, most preferably about 3 to 7% by weight. If higher amounts of prepolymer are desired, acid can be added to help prevent gel formation. Preferably the reaction is carried out from just above the freezing point of water to about room temperature. Higher temperature may be used, although they enhance the rate of gel formation. Glyphosate acid is added after the prepolymer/water reaction is complete. The amount of glyphosate used will depend upon the amount desired in the final formulation, and can generally vary from about 0.1% to above 60% by weight. The current commercial formulation employs about 36% glyphosate acid (41% as the isopropylamine salt). The addition of glyphosate acid results in the formation of a white slurry. The slurry is neutralized with any suitable base, preferably a hydroxide such as sodium, potassium or ammonium hydroxide, most preferably isopropylamine. Preferably sufficient base is added to form the monosalt, although the di and tri-salts can also be formed upon addition of additional base. A clear, stable solution is obtained. Surfactant can be added at any point after the reaction of the prepolymer with water, i.e., immediately prior to glyphosate addition, immediately prior to neutralization, or after neutralization. Preferably the amount of surfactant added is from about 0.1 to about 20% (wt/wt) of glyphosate, with the actual amounts depending upon the identify of the surfactant used. Upon evaporation of water, strong elastic films are obtained. These films are hydratable water-insoluble films which form after spray application of the formulation to the substrate. Such hydratable films are desirous since they prevent the crystallization of glyphosate on the surface of the leaf of the plant being sprayed. Such crystallizations readily occur in the absence of the polymer. These hydratable films also greatly enhance the rainfastness of the formulation.

In the second embodiment of the present invention, the prepolymer is incorporated into the formulation as a reaction product covalently bonded with glyphosate. Specifically, glyphosate acid is added directly to the prepolymer, and reacts with the free isocyanate groups present in the prepolymer to cap the same. Either partial or complete capping of the isocyanate groups can be obtained, depending upon the relative amount of glyphosate used. The resulting reaction product is neutralized with a suitable base as in the first embodiment. Surfactant can be added prior to or after neutralization. Amounts of constituents used are similar to those disclosed above with respect to the first embodiment.

In the third embodiment of the present invention, the hydrophilic isocyanate end-capped prepolymers are incorporated as a reaction product with a surfactant via a covalent linkage between the isocyanate (—NCO) groups of the polymer and reactive groups typically available on surfactants, such as reactive primary or secondary amine (—NH, —NH$_2$) groups, sulfhydryl (—SH) groups, hydroxyl (—OH) groups and carboxylate (—COOH) groups. As in the second embodiment, the capping of the free isocyanate groups in the prepolymer can be partial or complete, depending upon the relative amounts of reactants used. Preferably the surfactant is an alkyl ethoxylated amine that includes a mixture of polyethylene glycol, diethylene glycol and ethylene glycol. Glyphosate acid is then added, and the solution is neutralized with a suitable base. Amounts of constituents used are similar to those disclosed above with respect to the first embodiment.

The formulations of the present invention are preferably spray-applied to above-ground portions of the plants. The concentration of active ingredient should be present in a herbicidally effective amounts, which depends on the particular plant species and the desired response. Suitable concentrations of active ingredient for spray application are from about 0.07% to about 1%. In view of the enhanced rainfastness of the instant formulations as demonstrated by the following examples, substantially less active material is needed than was previously thought necessary.

EXAMPLE 1

At room temperature, 28 grams of HYPOL® PreMA® G-50 hydrophilic prepolymer were added to 972 grams of water. The solution was stirred for two hours to ensure complete reaction of the prepolymer with the water. 100 grams of glyphosate acid was added, and the pH was adjusted to 4.8 with isopropylamine. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 2

At room temperature, 30 grams of HYPOL® PreMA® G-50 hydrophilic prepolymer were added to a mixture of alkylamineethoxylate (62.5 g) and water (907.5 g). The solution was stirred for two hours. 150 grams of glyphosate acid was added and the solution was neutralized with isopropylamine to a pH of 4.8. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 3

At room temperature, 42 grams of a surfactant comprising about 50% tallow amine ethoxylate (15 moles ethoxylate), 20% polyethylene glycol (molecular weight 600) and 30% ethylene and diethylene glycol were added to 928 grams of water. 30 grams of HYPOL® PreMA® G-50 hydrophilic prepolymer were added and allowed to mix for two hours. 150 grams of glyphosate acid were added and the pH was adjusted with isopropylamine to 4.8. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 4

At room temperature, 62.5 grams of a surfactant comprising about 50% tallow amine ethoxylate (15 moles ethoxylate), 20% polyethylene glycol (molecular weight 600) and 30% ethylene and diethylene glycol were mixed with 877.5 grams of water. 60 grams of HYPOL® PreMA® G-50 were added to the mixture and allowed to stir for three hours. 150 grams of glyphosate acid were mixed for 30 minutes into the resulting solution. The slurry was neutralized with isopropylamine to a pH of 4.8. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 5

At room temperature, 42 grams of a surfactant comprising about 50% tallow amine ethoxylate (15 moles ethoxylate), 20% polyethylene glycol (molecular weight 600) and 30% ethylene and diethylene glycol were mixed with 897.5 grams of water. 60 grams of HYPOL® PreMA® G-50 were added to this mixture and the solution was stirred for two hours. 150 grams of glyphosate acid were then added and the slurry neutralized to a pH of 4.8 with isopropylamine. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 6

At room temperature, 28 grams of HYPOL® PreMA® G-50 hydrophilic prepolymer were added to 972 grams of water. The mixture was allowed to stir for 3 hours. 100 grams of glyphosate acid were added to this solution and the pH was adjusted to 4.8 with isopropylamine. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 7

At room temperature, 30 grams of HYPOL® PreMA® G-50 hydrophilic prepolymer were added to 907.5 grams of water. The solution was allowed to stir for 60 minutes. 150 grams of glyphosate acid were added, followed by 62.5 grams of Toximal TA-15 surfactant. The pH was adjusted from 2.85 to 4.1 with isopropylamine. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 8

At room temperature, 60 grams of HYPOL® PreMA® G-50 hydrophilic prepolymer were added to 870 grams of water. The solution was allowed to stir for 60 minutes. 150 grams of glyphosate acid were added, followed by 62.5 grams of Toximal TA-15 surfactant. The pH was adjusted to 3.85 with isopropylamine. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 9

At room temperature, 15 grams of glyphosate acid were slurried in 90 grams of water. 3 grams of HYPOL® PreMA® G-50 were added to this slurry and allowed to mix for one hour. 6 grams of Toximal TA-15 surfactant were then added and the contents neutralized to a pH of 4.0 with isopropylamine. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 10

At room temperature, 20 grams of glyphosate acid were slurried in 85 grams of water. 3 grams of HYPOL® PreMA® G-50 hydrophilic prepolymer were added to this slurry and allowed to mix for 61 minutes. 6 grams of Toximal TA-15 surfactant were then added and the contents neutralized to a pH of 4.7 with isopropylamine. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 11

At room temperature, 36 grams of glyphosate acid were slurried in 69 9rams of water. 3.3 grams of HYPOL® PreMA® G-50 hydrophilic prepolymer were added to this slurry and allowed to stir for 65 minutes. 6 grams of Toximal TA-15 surfactant were then added and the contents neutralized to a pH of 5.0 with isopropylamine. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 12

At room temperature, 62.5 grams of a surfactant comprising about 50% tallow amine ethoxylate (15 moles ethoxylate), 20% polyethylene glycol (molecular weight 600) and 30% ethylene and diethylene glycol were stirred into 907.0 grams of water. 60 grams of HYPOL® PreMA® G-50 hydrophilic prepolymer were added to this mixture and the contents were allowed to mix for 47 minutes. 109.6 grams of glyphosate acid were then added and the contents were neutralized to a pH of 4.75 with isopropylamine. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 13

At room temperature, 30 grams of HYPOL® PreMA® G-50 hydrophilic prepolymer were mixed for 45 minutes with 907.5 grams of water. 42 grams of a surfactant comprising about 50% tallow amine ethoxylate (15 moles ethoxylate), 20% polyethylene glycol (molecular weight 600) and 30% ethylene and diethylene glycol were then added and the solution was mixed for another 45 minutes. 109.6 grams of glyphosate acid were added, and the contents neutralized to a pH of 4.64 with isopropylamine. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 14

Figure 2:
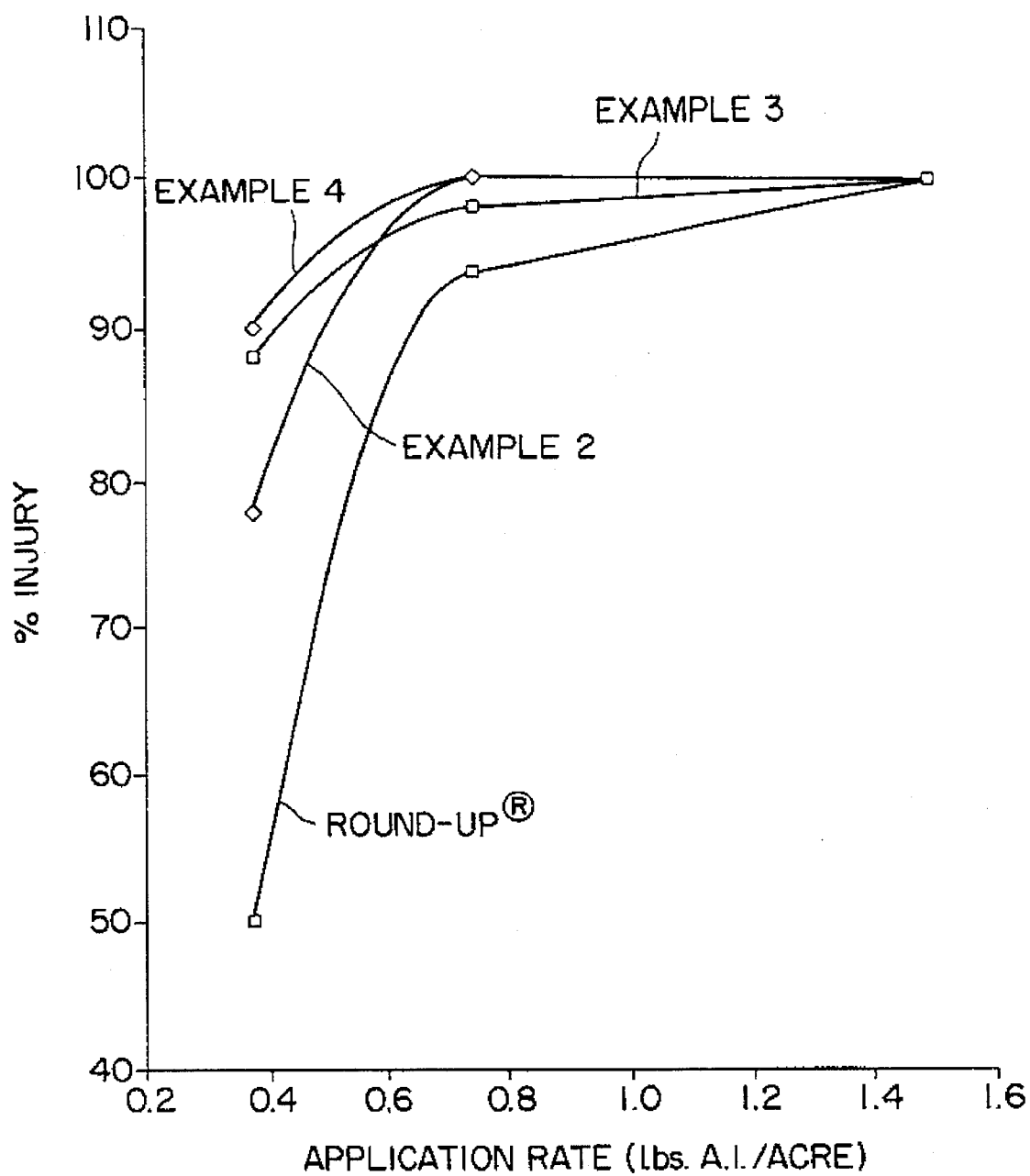
FIG. 2 is a graph comparing dose response of formulations of the present invention to commercial grade Round-up® herbicide after 42 days.

A dose response study was conducted during the summer/fall months to evaluate the efficacy of the present invention, and the results are shown in FIGS. 1 and 2. The experimental design was a randomized complete block with four replications. Plant injury was evaluated visually every week during the study.

Bermudagrass was sprayed with the formulations of Examples 2, 3 and 4, as well as the commercial grade Round-up®, at 0.375, 0.75 and 1.5 lb of active ingredient per acre. Commercial Round-up® effectively controlled Bermudagrass at the two higher rate applications (0.75 and 1.5 lb/acre). At these higher concentrations, all the formulations shown in FIGS. 1 and 2 demonstrated a high degree of injury to Bermudagrass. Shoot fresh weight data confirmed the injury ratings. The formulations of the present invention were more effective in reducing Bermudagrass shoot weight than commercial Round-up® when applied at 0.375 lb/acre, and were virtually equivalent to Round-up® herbicide at the two higher concentrations.

EXAMPLE 15

Figure 3:
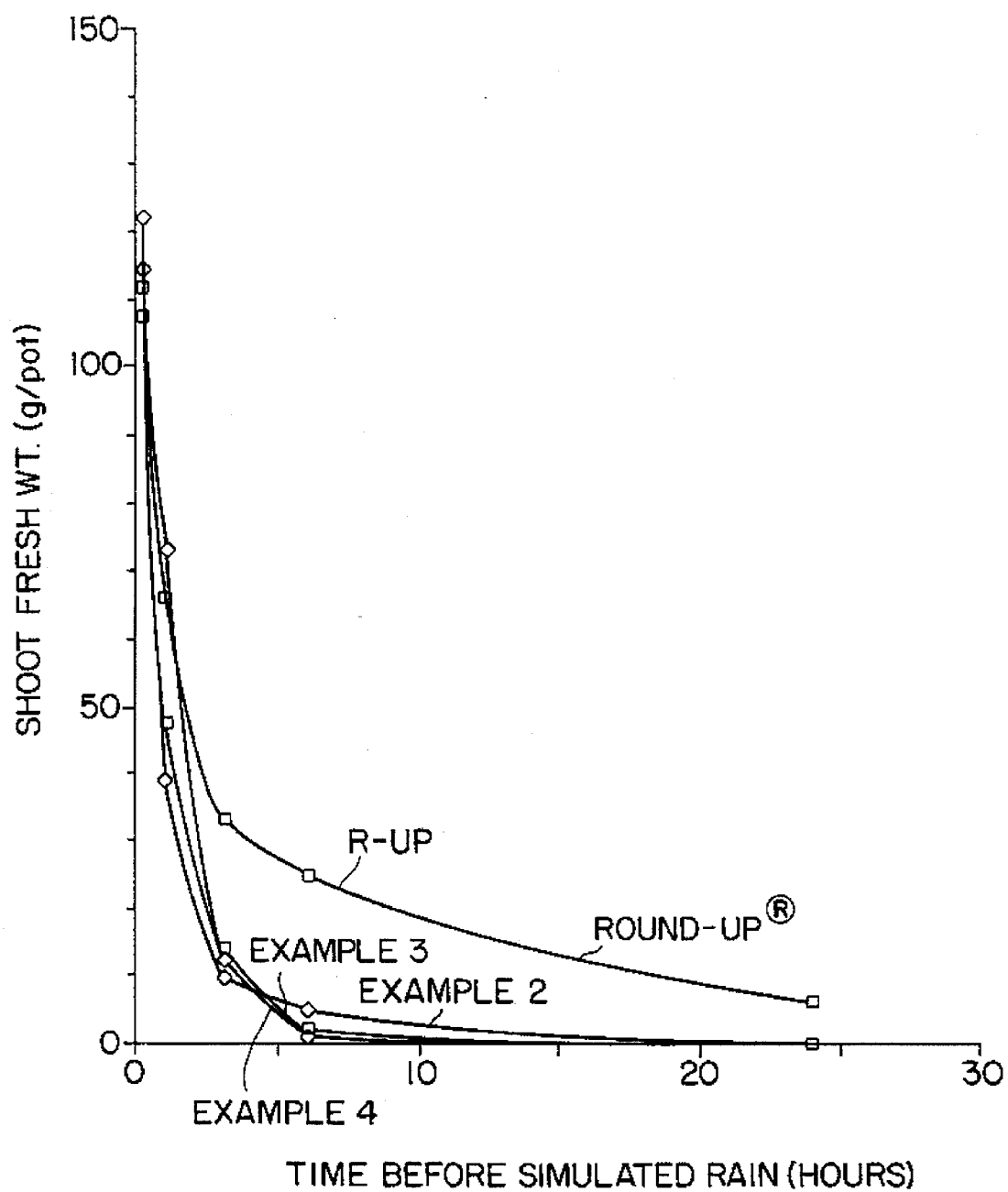
FIG. 3 is a graph comparing shoot fresh weight of Bermudagrass after application of formulations of the present invention and of commercial grade Round-up® herbicide after 70 days.

A simulated rainfall was applied at 15 minutes, 1 hour, 3 hours, 6 hours and 24 hours after formulation application, and the results are shown in FIG. 3. The formulations of Examples 2, 3 and 4 of the present invention significantly outperformed commercial Round-up® herbicide.

EXAMPLE 16

Samples from Examples 2, 3 and 4 above were sprayed in a tropical environment to test the efficacy in hot humid conditions. The samples were sprayed in 2 meter×20 meter plots, with a 1 meter plot buffer zone maintained between plots. Plots were marked with string and stakes.

The weed variety in the plots was noted prior to application and was defined as follows:

30–40% broadleaf

58–68% grasses

2% elusive indica

Climatic conditions during spray application were noted as follows:

Temperature: 30° C.

Humidity: 75%

Full sun on numbered plots

Light to zero wind

Little weather change over two hour spray time

A Solo motorized pump spray (air pressured) was employed to spray the plots. A fan jet 564 nozzle and a walking speed of 40 meters/minute was noted. 2 kg pressure was measured in the tank.

Duplicate samples were tested for both dosage response and rainfast properties. The plots were observed after 3 weeks, and all weeks were completely dead. The dosage response and rainfast results are as follows at a 3-month interval:

TABLE 1

DOSAGE RESPONSE

| SAMPLE | RATE (1/hectare) | VISUALS/WEEDS REMAINING |
| --- | --- | --- |
| Example 2 | 4.5 | Some broadleaf 60–70% kill No grass regrowth, 85–98% kill |
| Example 3 | 4.5 | About 50–60% broadleaf kill No grass regrowth, 95–98% kill |
| Example 4 | 4.5 | Very few broadleaves remain, 94–95% kill, 5–6% regrowth. No grass regrowth, 100% kill |
| SPARK ® | 6 | 70% regrowth of broadleaf, 30% kill 25–35% grasses regrow |
| ROUND-UP ® | 4.5 | Almost total regrowth of all weeds |

TABLE 2

RAINFASTNESS

| SAMPLE | RATE (1/hectare | WATER TIME AFTER SPRAYING | VISUALS |
| --- | --- | --- | --- |
| Example 2 | 4.5 | 1.5 hours | Some regrowth |
| Example 3 | 4.5 | 1.5 hours | No grass regrowth; |

TABLE 2-continued

| | RAINFASTNESS | | |
|---|---|---|---|
| SAMPLE | RATE (l/hectare | WATER TIME AFTER SPRAYING | VISUALS |
| Example 4 | 4.5 | 1.5 hours | some broadleaf regrowth Only two broadleaf plants found in plot. No grasses found. Essentially complete kill. |

The watered plots were also observed after 3 weeks of spraying. The grasses in the plots were only yellow and were not yet brown or dead.

At the end of 6 weeks, all weeds in all plots were dead. At 6–7 months, preliminary data indicated that plots sprayed with samples from Examples 2, 3 and 4 were still exhibiting herbicidal activity and little regrowth was observed.

EXAMPLE 17

In another plot, the sample from Example 4 was sprayed. The plot was split in half, with the second half only being watered at 1.5 hours after spraying at an approximate rate of 10 liters/plot of water to simulate rainfall. After 6 weeks, all weeds in both plots were dead. At 3 months, both sides of the plot were equally dead. No difference between the watered and unwatered side was observed.

EXAMPLE 18

Two grams of HYPOL® 2000 prepolymer were added to 95 g of water. The solution was stirred for 50 minutes. Two grams of lauroyl sodium sarcosinate were then added to the solution. Twelve grams of glyphosate acid were added and the solution was neutralized with isopropylamine to a pH of approximately 4.8. A clear colorless solution exhibiting some viscosity was obtained.

EXAMPLE 19

Into 98 grams of water, 5 grams of glyphosate acid were added. After 30 minutes of stirring, 2 grams of HYPOL® 2000 prepolymer were added. The solution was then neutralized with 10% wt/wt sodium hydroxide to a pH of 4.3. A clear, stable solution was formed that was very liquid, indicating the compatibility of the components.

EXAMPLE 20

Three grams of HYPOL® PreMA® G-50 hydrophilic prepolymer were added to 97 grams of water and the solution was heated uniformly from 27° C. to 46° C. over 30 minutes. The solution thickened but did not gel. The contents were stirred on a cold magnetic stir plate for another 34 minutes. At 36° C., 5 grams of glyphosate acid were added and the contents neutralized with isopropylamine to a pH of 4.6.

The contents were split in half, with one half stored as a retainer and the other dried in a fume hood over 5 hours. A thin tough film formed which rehydrated, upon the addition of water, to a thick undissolvable skin. The contents were covered and allowed to stand overnight at room temperature. The skin did not redissolve.

EXAMPLE 21

Eighteen grams of Toximal TA-15 surfactant were dissolved in water over a period of 1 hour. 2.8 grams of HYPOL® PreMA® G-50 hydrophilic prepolymer were added to the solution and allowed to mix for 180 minutes. 20 grams of glyphosate acid were added and the solution was neutralized with isopropylamine from a pH of 1.96 to 4.21. A stable, clear solution with a brownnish color (imparted by the surfactant) was obtained.

EXAMPLE 22

Thirty-six grams of glyphosate acid were added to 69 grams of water. 3.3 grams of HYPOL® PreMA® G-50 hydrophilic prepolymer were then added and the solution was allowed to stir for 20 minutes. The solution was neutralized to a pH of 5.00 with isopropylamine. The solution appeared very slightly cloudy but did not separate, indicating all components at this concentration to be compatible.

EXAMPLE 23

125 grams of 50% tallow ethoxylated amine (15 ethoxy equivalent), 20% polyethylene glycol 600, and 30% diethylene glycol/ethylene glycol was added to 1814.0 grams of water. 120 grams of HYPOL® PreMA® G-50 hydrophilic prepolymer were added and the solution was allowed to stir for 58 minutes. 219.2 grams of glyphosate acid were then added and the pH neutralized to 4.79 with isopropylamine. The temperature was recorded at 34° C. at this point. A clear stable solution was obtained.

What is claimed is:

1. A herbicidal composition, comprising a solution of a herbicidally effective amount of a member selected from the group consisting of N-phosphonomethylglycine, a herbicidally active derivative of N-phosphonomethylglycine, and mixtures of N-phosphonomethylglycine and a herbicidally active derivative of N-phosphonomethylglycine; an effective amount of an activating surfactant; and a hydrophilic polymer selected from the group consisting of polyureaurethane, polyurea and polyurethane.

2. The herbicidal composition of claim 1, wherein said hydrophilic polymer is formed from a prepolymer selected from the group consisting of toluene diisocyanate-polyethylene glycoltimethylolpropane, methylene diisocyanate-methylene diisocyanate homopolymmer-polymeric methylene diisocyanate-polyethylene glycol, toluene diisocyanate and polymer of ethylene oxide and propylene oxide with trimethylolpropane, isophorone diisocyanate and polymer of ethylene oxide-propylene oxide-trimethylolpropane, toluene diisocyanate polyethylene glycol trilactate, and polyethylene glycol end capped with toluene diisocyanate.

3. The herbicidal composition of claim 1, wherein said surfactant is selected from the group consisting of alkylbenzene and alkyl naphthalene sulfonates, alkyl phenol polyoxyethylene, sulfated fatty alcohols, amines, acid amides, long chain acid esters of sodium isethionate, esters of sodium sulfosuccinate, sulfated or sulfonated fatty acid esters, petroleum sulfonates, N-acyl sarcosinates, alkyl polyglycosides, and alkyl ethoxylated amines.

4. The herbicidal composition of claim 3, wherein said surfactant is a mixture of about 1–100% tallow amine ethoxylate, 1–50% polyethylene glycol, and 0–50% ethylene and diethylene glycol.

5. The herbicidal composition of claim 1, further comprising an additive selected from the group consisting of polyethylene glycol, diethylene glycol, ethylene glycol, methanol, ethanol, 2-propanol, n-propanol, butanol, hexanol and heptanol.

6. The herbicidal composition of claim 1, further comprising a herbicidal effective amount of a member selected from the group consisting of phenoxy acids, phenoxy esters, phenoxy salts, benzoic acid, aryloxy phenoxypropionate acid, aryloxy phenoxypropionate ester, aryloxy phenoxypropionate salts, sulfonyl ureas, imidazilinones, bipyridillium, diphenyl ether, cyclohexanedione, methane arsonate, triazines, aliphatic carboxylic acids, benzonitrile, carbamate and thiocarbamate.

7. A method of controlling weeds, comprising administering to said weeds or the locus thereof an effective amount of a solution comprising a herbicidally effective amount of a member selected from the group consisting of N-phosphonomethylglycine, a herbicidally active derivative of N-phosphonomethylglycine, and mixtures of N-phosphonomethylglycine and a herbicidally active derivative of N-phosphonomethylglycine; an effective amount of an activating surfactant; and a hydrophilic polymer selected from the group consisting of polyurea-urethane, polyurea and polyurethane.

8. The method of claim 7, wherein said surfactant is selected from the group consisting of alkyl benzene and alkyl naphthalene sulfonates, alkyl phenol polyoxyethylene, sulfated fatty alcohols, amines, acid amides, long chain acid esters of sodium isethionate, esters of sodium sulfosuccinate, sulfated or sulfonated fatty acid esters petroleum sulfonates, N-acyl sarcosinates, alkyl polyglycosides, and alkyl ethoxylated amines.

9. The method of claim 8, wherein said surfactant is a mixture of about 1–100% tallow amine ethoxylate, 1–50% polyethylene glycol, and 0–50% ethylene and diethylene glycol.

10. A delivery system for delivering a herbicidal composition, said delivery system comprising a solution of a hydrophilic polymer selected from the group consisting of polyurea-urethane, polyurea and polyurethane, a herbicidally effective amount of a herbicide selected from the group consisting of N-phosphonomethylglycine, a herbicidally active derivative of N-phosphonomethylglycine, and mixtures of N-phosphonomethylglycine and a herbicidally active derivative of N-phosphonomethylglycine, and an activating surfactant, said activating surfactant being a mixture of about 1–100% tallow amine ethoxylate, 1–50% polyethylene glycol, and 0–50% ethylene and diethyletene glycol.

11. A method of formulating a solution of a herbicidal composition, comprising forming a reaction product of a hydrophilic polymer formed from a prepolymer selected from the group consisting of polyurea-urethane, polyurea and polyurethane and water; adding to said reaction product a herbicidally effective amount of N-phosphonomethylglycine to form a slurry; and neutralizing the resulting slurry with a base.

12. The method of claim 11, further comprising adding surfactant before or after said addition of said N-phosphonomethylglycine.

13. A method of formulating a herbicidal composition, comprising forming a reaction product of a hydrophilic polymer formed from a prepolymer selected from the group consisting of polyurea-urethane, polyurea and polyurethane, and N-phosphonomethylglycine, and neutralizing said reaction product with a base.

14. The method of claim 13, further comprising adding surfactant before or after said neutralization.

15. A method of formulating a solution of a herbicidal composition, comprising forming a reaction product of a hydrophilic polymer formed from a prepolymer selected from the group consisting of polyurea-urethane, polyurea and polyurethane and an activating surfactant; adding to said reaction product a herbicidally effective amount of N-phosphonomethylglycine, and neutralizing the resulting solution with a base.

16. The method of claim 15, further comprising adding surfactant before or after said neutralization.

17. A method of formulating a solution of a herbicidal composition, comprising forming a reaction product of a hydrophilic polymer formed from a prepolymer selected from the group consisting of polyurea-urethane, polyurea and polyurethane and an activating surfactant; and adding to said reaction product a herbicidally effective amount of a herbicidally active derivative of N-phosphonomethylglycine.

* * * * *